United States Patent
Scherer et al.

[11] Patent Number: 5,789,670
[45] Date of Patent: Aug. 4, 1998

[54] RAIN SENSOR

[75] Inventors: Michael Scherer, Rodenbach; Roland Werner, Hainburg, both of Germany

[73] Assignee: Leybold Aktiengesellschaft, Hanau, Germany

[21] Appl. No.: 797,978

[22] Filed: Feb. 12, 1997

Related U.S. Application Data

[62] Division of Ser. No. 490,725, Jun. 15, 1995, Pat. No. 5,653,855.

[30] Foreign Application Priority Data

Aug. 4, 1994 [DE] Germany .......................... 44 27 627.3

[51] Int. Cl.$^6$ .................................................. G01W 1/00
[52] U.S. Cl. ............................................... 73/170.17
[58] Field of Search ....................... 73/170.17; 324/65 R

[56] References Cited

U.S. PATENT DOCUMENTS

| | | | |
|---|---|---|---|
| 4,393,434 | 7/1983 | Imai et al. | |
| 4,797,605 | 1/1989 | Palanisamy | 324/65 R |
| 4,831,493 | 5/1989 | Wilson et al. | 361/286 |
| 5,254,371 | 10/1993 | Hegner et al. | 427/487 |
| 5,395,740 | 3/1995 | Swirbel et al. | |

FOREIGN PATENT DOCUMENTS

| | | |
|---|---|---|
| 411229 | 2/1991 | European Pat. Off. |
| 507491 | 7/1992 | European Pat. Off. |
| 2656422 | 6/1991 | France |
| 4011782 | 1/1979 | Japan |
| 8092944 | 6/1983 | Japan |
| 62-247238 | 10/1987 | Japan |
| 3106548 | 5/1988 | Japan |
| 2293688 | 12/1990 | Japan |
| 8907264 | 8/1989 | WIPO |

*Primary Examiner*—William L. Oen
*Attorney, Agent, or Firm*—Felfe & Lynch

[57] ABSTRACT

In a moisture sensor (1), the effective sensor field (4) is formed by two sensor elements (8a, 8b,) having interdigitating parallel tracks. These sensor elements consist of layers of a metal nitride compound, especially a chromium-nitrogen compound, deposited by means of magnetron cathode sputtering or glow discharge onto a dielectric substrate (2), the metal nitride layers being deposited onto the substrate surface which has first been cleaned by ion sputtering. These sensor element layers (8a, 8b) have a high hardness of about 2,000 on the Vickers scale, as a result of which the sensor elements (8a, 8b) are highly resistant to abrasive wear such as that caused by windshield wipers or scratching from ice. The moisture sensor can be produced with a low electrical surface resistivity of <100 ohms☐ and is chemically stable with respect to environmental effects such as salt water and/or windshield cleaning fluids. As a result, the proposed moisture sensor is especially suitable for use as a rain sensor on vehicles, the rain sensor preferably being mounted on a window of the vehicle.

10 Claims, 1 Drawing Sheet

RAIN SENSOR

This application is a divisional of Application Ser. No. 08/490,725 filed June. 15, 1995; now U.S. Pat. No. 5,653,855.

BACKGROUND OF THE INVENTION

The invention pertains to a process for the production of a moisture sensor of the type comprising two electrically conductive elements arranged on a dielectric substrate to form a sensor field which undergoes a change in impedance when wet.

Moisture sensors of this type and also methods for their production are already known. For example, in EP 0 507 491 A2, a process for the production of a rain sensor installed on a vehicle window is described. This sensor consists essentially of two electrically conductive surfaces intermeshing like fans, which are attached to a glass plate to form a resistance element. The change in the impedance of this resistance element caused by the presence of moisture on the surface of the sensor is recorded electronically and forms the sensor output variable. The two conductive surfaces consist of a metal oxide layer, which is deposited pyrolytically on the glass substrate. After the forming of the glass substrate, the final surface structure is produced by means of, for example, laser etching or a chemical etching process based on the use of a photomask.

A disadvantage of moisture sensors produced in this way is that the conductivity of the metal oxide layer, e.g., a layer of tin oxide, is significantly reduced by the forming process, normally carried out at about 600° C., and by the following process of tempering the glass plate, and the sensitivity of the sensor is reduced.

SUMMARY OF THE INVENTION

The invention is based on the task of creating a moisture sensor of the type described above which does not suffer from the disadvantages indicated above and which, in addition, adheres very strongly to the substrate, is highly resistant to the abrasive wear, and is also chemically stable with respect to environmental influences. A further task of the invention is to provide a process for producing a moisture sensor of this type.

For a moisture sensor according to the invention, the conductive surfaces (sensor elements) are deposited under vacuum onto the substrate surface (glass surface), which has been cleaned by ion bombardment and thus activated for the following coating step. The structure of the sensor field, consisting of at least two sensor elements, is produced by means of a photomask technique. For this purpose, a photoresistive layer is applied to the dielectric substrate, dried, and covered by a photomask corresponding to the sensor structure. The photoresist is exposed to light and then developed. The unexposed parts of the photoresist are dissolved away by the developer, and thus a negative image of the sensor field is obtained. The subsequent cleaning of the bared substrate areas by means of ion bombardment offers the advantage that loosened impurities on the substrate can be completely removed, and impurities which could recontaminate the surface of the substrate before the next process step, i.e., the application of the conductive layer, are prevented from settling back on the substrate. In addition, the ion bombardment has the advantageous effect of activating the surface of the substrate to be coated, which helps to increase strength with which the conductive layer adheres to the substrate.

According to the invention, this ion-sputtering cleaning process can be carried out either by means of a glow-discharge in a noble gas, and preferably argon and/or $O_2$ gas or by means of a high-frequency sputter-etching process. The process parameters to be used in these cases have the following values:

$P_{argon} = 2 \times 10^{-3}$ mbar;

$P_{HF} = 900$ W;

$U_{DC} = 550$ V; and $t = 60$ sec.

The sensor-forming layer to be applied after the cleaning of the negative substrate structure is preferably deposited by reactive magnetron sputtering onto the substrate. A metal nitride compound, preferably a chromium-nitrogen compound, is selected as the sensor-forming layer. Reactive DC magnetron sputtering of $CrN_x$ in an argon/nitrogen atmosphere has been found especially advantageous. The DC magnetron sputtering process can be carried out advantageously with the following process parameter values:

$P_{sputtering} = 6 \times 10^{-3}$ mbar;

$P_{DC} = 4$ kW;

$t = 20$ sec.

The chromium nitride layer thus produced contains chromium and nitrogen in a ratio of 55:45%; the layer of $d_{CrNx}$ is 100 nm thick; and the surface resistivity $R_\square$ is 50 ohms/□. By the use of other values for the process parameters, it is possible to deposit layers in thicknesses ranging from 20 to 500 nm, and preferably 100 nm, onto the substrate. For the electrical surface resistivity $R_\square$, values of less than 300 ohms/□, preferably values of less than 100 ohms/□, are suitable. Decreasing the electrical surface resistivity has the advantage of increasing the sensitivity of the sensor. It is advantageous for the metal nitride layer also to contain oxygen.

In the final step of the process, the exposed photoresist layer still adhering to the substrate (preferably a glass substrate) is removed by a wet chemical treatment.

The chromium nitride layers deposited in this way on the glass substrate are surprisingly very hard, offering a hardness of about 2,000 on the Vickers scale, and are chemically stable with respect to environmental effects, especially those exerted by air pollution, salt water, alternating temperature stresses, and glass cleaners. In combination with the high resistance to abrasive wear imparted by its hardness, a moisture sensor of this type is suitable especially for use as a rain sensor on the outside surface of a vehicle window exposed to severe abrasive wear from the effects of windshield wipers, from scratching by ice, and from impacts by various types of hard particles.

DETAILED DESCRIPTION OF THE PREFERRED EMBODIMENT

Figure 1:
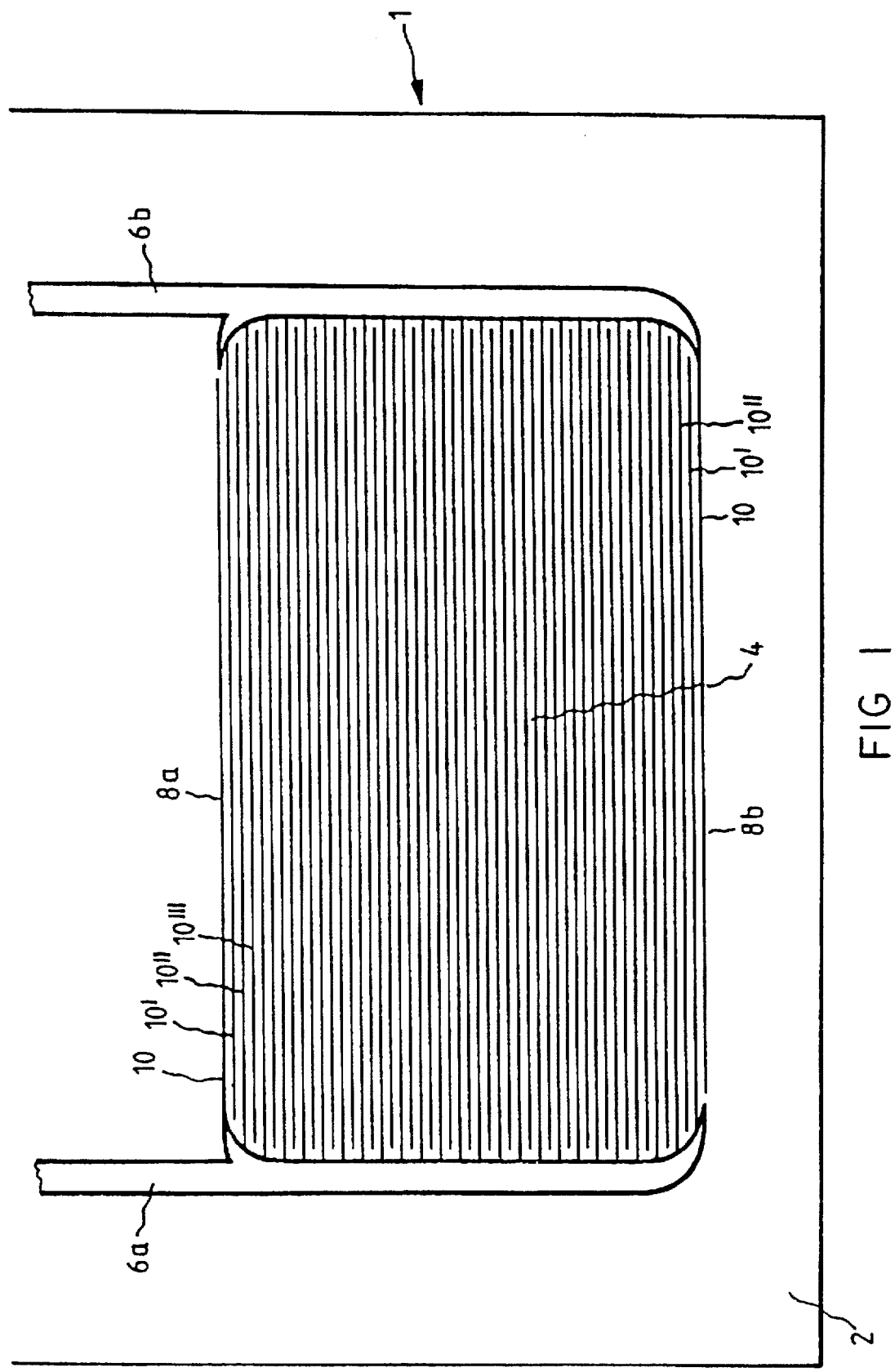
FIG. 1 is a schematic plan view of the sensor according to the invention.

A moisture sensor 1, shown in FIG. 1, consists essentially of two flat sensor elements 8a, 8b, which are mounted on a common dielectric substrate 2. The individual sensor elements 8a, 8b consist of parallel conductive tracks 10, 10', 10", 10''', . . . , each of which is connected conductively at its end to an electric terminal 6a, 6b. The free ends of conductive tracks 10, 10', 10", 10''', . . . of individual sensor elements 8a, 8b interdigitate conductive tracks 10, 10", . . . of sensor element 8a alternating in parallel fashion with conductive tracks 10', 10'" of sensor element 8b. When sensor field 4 is wetted by, for example, a drop of water, the electrical resistance between sensor elements 8a and 8b changes. This change in impedance can be recorded by a suitable electronic sensor unit (not shown in FIG. 1) connected to electrical terminals 6a, 6b and can be used for a subsequent control purpose such as for turning on a windshield wiper motor.

What is claimed is:

1. Moisture sensor comprising a dielectric substrate, and two electrically conductive sensor elements arranged on said substrate adjacent to each other but insulated from each other, said sensor elements comprising a metal nitride layer.

2. Moisture sensor as in claim 1 wherein said metal nitride is chromium nitride.

3. Moisture sensor as in claim 1 wherein said metal nitride contains oxygen.

4. Moisture sensor as in claim 1 wherein said metal nitride layer is 20–500 nm thick.

5. Moisture sensor as in claim 4 wherein said metal nitride layer is 100 nm thick.

6. Moisture sensor comprising a dielectric substrate, and two electrically conductive sensor elements arranged on said substrate adjacent to each other but insulated from each other, said sensor elements comprising a metal nitride layer, wherein said metal nitride layer has a surface resistivity of less than 300 ohms/□.

7. Moisture sensor as in claim 6 wherein said metal nitride layer has a surface resistivity of less than 100 ohms/□.

8. Moisture sensor as in claim 1 wherein said substrate is glass.

9. Moisture sensor as in claim 1 wherein each sensor comprises a plurality of parallel tracks which interdigitate with parallel tracks of the other sensor.

10. Moisture sensor as in claim 1 wherein said metal nitride layers of said electrically conductive sensor elements each have a respective exposed electrically conductive surface disposed so that moisture contacting the moisture sensor engages the exposed surfaces and provides an electrical connection therebetween.

* * * * *